(12) United States Patent  
Jones (10) Patent No.: US 8,840,583 B2  
(45) Date of Patent: Sep. 23, 2014

(54) SAFETY SYRINGE

(75) Inventor: John Jones, Fresno, CA (US)

(73) Assignee: Syringex Medical, Inc., New York, NY (US)

( * ) Notice: Subject to any disclaimer, the term of this patent is extended or adjusted under 35 U.S.C. 154(b) by 363 days.

(21) Appl. No.: 13/211,217

(22) Filed: Aug. 16, 2011

(65) Prior Publication Data

US 2013/0046251 A1  Feb. 21, 2013

(51) Int. Cl.
- *A61M 5/00* (2006.01)
- *A61M 5/34* (2006.01)
- *A61M 5/32* (2006.01)

(52) U.S. Cl.
CPC ............... *A61M 5/322* (2013.01); *A61M 5/347* (2013.01); *A61M 2005/323* (2013.01)
USPC .......................................... 604/110; 604/187

(58) Field of Classification Search
USPC .................... 604/110, 195, 164.01, 187, 192
See application file for complete search history.

(56) References Cited

U.S. PATENT DOCUMENTS

| | | | |
|---|---|---|---|
| 4,507,117 A | 3/1985 | Vining et al. | |
| 4,675,005 A | 6/1987 | DeLuccia | |
| 4,692,156 A | 9/1987 | Haller | |
| 4,710,170 A | 12/1987 | Haber et al. | |
| 4,747,830 A | 5/1988 | Gloyer et al. | |
| 4,790,822 A | 12/1988 | Haining | |
| 4,804,370 A | 2/1989 | Haber et al. | |
| 4,826,484 A | 5/1989 | Haber et al. | |
| 4,883,471 A | 11/1989 | Braginetz et al. | |
| 4,919,652 A | 4/1990 | Alter et al. | |
| 4,986,813 A | 1/1991 | Blake, III et al. | |
| 5,112,316 A | 5/1992 | Venturini | |
| 5,336,198 A | 8/1994 | Silver et al. | |
| 5,458,576 A | 10/1995 | Haber et al. | |
| 2002/0065489 A1 | 5/2002 | Novacek et al. | |
| 2004/0054332 A1 | 3/2004 | Ferguson | |
| 2004/0106903 A1* | 6/2004 | Shue et al. | 604/168.01 |
| 2008/0033355 A1 | 2/2008 | Mazzara | |

OTHER PUBLICATIONS

International Search Report and Written Opinion dated Jan. 2, 2013 in corresponding International Application No. PCT/US2012/050776 filed Aug. 16, 2011, 13 pages.

\* cited by examiner

*Primary Examiner* — Kami A Bosworth (74) *Attorney, Agent, or Firm* — Dentons US LLP (57) ABSTRACT

A retractable syringe, comprising a needle having a tip and a base, a needle collar coupled to the needle, the needle collar including at least one groove disposed in a bottom portion of the needle collar and extending from the portion of the needle collar nearest to the base of the needle toward the tip of the needle, a fitting coupled to the needle collar and including a sealing element disposed between a first portion of the fitting and the needle collar, a barrel unit, the barrel unit designed for coupling to the fitting, a plunger unit having a piston on a first end of the plunger unit, the plunger unit and piston being positioned in the barrel unit, an extractor element coupled to the first end of the plunger and having a proximal end adjacent to the plunger and a distal end, the extractor element designed for coupling to the needle collar and encompassing at least a portion of the at least one groove.

52 Claims, 10 Drawing Sheets

SAFETY SYRINGE

FIELD OF THE INVENTION

The field of the present invention relates to safety syringes.

BACKGROUND OF THE INVENTION

A typical hypodermic syringe includes a transparent cylindrical barrel, generally open at a proximal end, a plunger assembly movable within the barrel to dispense medication, and a needle assembly removably attached to the barrel at a distal end by means of a locking mechanism, such as Luer lock or Luer slip. During usage, medication is sealed within open side of the barrel by means of a rubber piston slipped over the distal end of the plunger. At the distal end of the syringe, sealing is accomplished through a sealant, such as an epoxy resin, extending between the outer surface of the needle and the lock hub carrying the needle. This sealant, and the locking mechanism fastening the needle assembly to the barrel, are also used to transmit the force, which may be as high as several pounds, required to insert the needle into the patient's body and to remove the needle after the injection process is complete. The applications of hypodermic syringes within a health care facility require the availability of syringes varying particularly in needle length and diameter, and in the dosage capacity of the barrel. To satisfy this need, needles and the remaining portions of syringes are made commercially available both as assembled units, and as separate units allowing the attachment of a selected one of the various needle assemblies to a selected one of various barrels. The Luer lock fittings used to fasten the needle to the barrel form a basis for It is thus desirable that any improved design for hypodermic syringes should include the capability of switching needles among the syringes. It is even more desirable that any improved design for hypodermic syringes should be capable of using standard needle assemblies, and that the new needle assemblies should be usable in standard syringe barrels.

Modern medical practice dictates that, in order to eliminate a possible source of contagious disease, hypodermic syringes are used only once. There is a growing concern, even when syringes are discarded immediately after use, that health care workers may be accidentally stuck by a hypodermic needle which has been used in the treatment of a patient having a serious communicable disease, such as AIDS or hepatitis. Used hypodermic needles have become an especially dangerous form of waste material, posing a danger to anyone handling trash from a health care facility and to anyone who might come into contact with such material after it has been dumped, and requiring special puncture resistant containers for disposal.

Another problem commonly associated with discarded hypodermic syringes is their potential use by drug abusers, who sometimes search waste material from health facilities for such devices. This practice obviously carries a significant risk of infection to these drug users and to others they may subsequently contact.

Conventional hypodermic syringes included an inward extending ring near the proximal opening of the barrel, which forms a stop, preventing the inadvertent removal of the plunger from the barrel. However, this ring is generally not rigid enough to prevent the deliberate, surreptitious removal of the plunger, as by a drug abuser.

One prior art solution to the aforementioned problems has been to enclose the needle in a sheath manually slipped over the needle end before and after use of the syringe. However, this technique still exposes health workers to the risk of being stuck with an infected needle as the sheath is slipped on, particularly when the needle is not properly aligned with the sheath opening. Furthermore, this technique does nothing to render the syringe useless to a drug abuser.

Another prior art solution to the aforementioned problems is breaking the needle from the syringe once it is used. While this procedure is followed in a number of health care facilities, there are still several disadvantages to this procedure. First, the broken needles are not necessarily enclosed in a way permitting their subsequent safe handling, and second, the additional handling of used needles by health care workers in the process of breaking the needles may increase the risk of their being accidentally stuck by an infected needle.

One attractive solution to the aforementioned problems is in providing a syringe/needle assembly in which the needle may be retracted into the barrel of the syringe after use, so that the needle is held in an envelope formed by the barrel during disposal. The patent literature includes descriptions of devices of a first general type, in which a needle is fastened to a needle carrier which travels axially within the barrel. In its distal position, the carrier holds the needle ready for use at the distal end of the barrel. After the plunger assembly is moved to the distal end of the barrel, after dispensing the desired medication, the plunger assembly engages and locks onto the needle carrier. When the plunger assembly is subsequently withdrawn and returned to the proximal end of its travel, the needle is carried with the plunger until it is completely enclosed within the barrel. At this point, the syringe ready for proper and safe disposal. Examples of syringes of this type are found in U.S. Pat. No. 4,710,170, issued to Haber et al on Dec. 1, 1987; in U.S. Pat. No. 4,790,822, issued to Haining on Dec. 13, 1988; and in U.S. Pat. No. 4,883,471, issued to Braginetz et al on Nov. 28, 1989.

In the prior art devices, the needle is fastened to the needle carrier by conventional means. For example, needle may be fastened to a Luer lock hub, which, in turn, is screwed onto a threaded hole forming internal surfaces in the needle carrier. Thus, syringes of this kind have the advantage of being capable of using standard needle assemblies of the types widely available for syringes not incorporating the safety feature of needle retraction. If the syringe is provided with its needle carrier at the distal position, an interchangeable needle may be screwed into the syringe from the distal end, in the conventional manner. However, the barrels of syringes of this type, of necessity, have relatively large openings at their distal ends, to accommodate the motion of the needle, together with a portion of the needle carrier as it is retracted into the barrel. This large opening, in turn, significantly increases the complexity and cost of the device by requiring fluid tight sealing around the outside of the needle carrier, so that medicine can be dispensed through the needle without leakage out of the distal end of the syringe.

Furthermore, the needle carrier of the prior art devices occupies a significant portion of the axial length of the barrel. The conservation of distance along this length is especially important in a syringe having a retractable needle because the space is needed for storage of the needle after use. Conventional syringes are built to particular sizes for convenient handling and use, as well as for various barrel capacities for medication. For example, the barrels of typical syringes having either three cubic centimeter and five cubic centimeter capacities are about 2.5 inches in length, with the difference in capacity being accomplished by varying the diameter. A typical long needle extends 1.5 inches from the end of the Luer hub to which it is attached. Including this hub, the length of the needle assembly is about 2.125 inches. Thus, the use of a needle carrier of the prior art requires lengthening the barrel beyond the length necessary for handling and capacity, thereby decreasing the ease and familiarity with which the syringe is handled and further increasing its costs of manufacture and distribution.

The device of U.S. Pat. No. 4,883,471 to Braginetz et al mounts the needle carrier in a second piston. After the medication is dispensed, vent ports are opened by rotating a cap at the distal end of the syringe, so that the atmosphere is allowed to enter the syringe at the distal end of this second piston. The retraction of the piston, with the needle, is then accomplished by the differential pressure established as the plunger is withdrawn. However, rotating the cap in this way presents the health care worker with the inconvenience of an extra step in the process.

The patent literature also describes devices of a second general type, in which the needle assembly is loaded into the syringe barrel from inside the barrel, to stick outward through a relatively small opening in the distal end of the barrel. After the injection of medicine by means of the plunger assembly, the needle assembly is attached to the distal end of the plunger assembly to be retracted into the syringe barrel as the plunger assembly is pulled back toward the proximal end of the barrel.

While syringes of this type address the concerns expressed above relative to the use of a separate needle carrier, they lack the important ability to use conventional needle assemblies, which are adapted to be screwed into place using Luer couplings from outside the distal end of the barrel. In addition, if interchangeable needles are to be used in any way on the syringes, they must be attached by relatively difficult or complex means within the barrels. Further, by changing a needle through the barrel, the sterility of the barrel can be violated.

Some devices of this second general type, in which the needle is loaded from inside the barrel, include couplings between the needle assemblies and the distal ends of the barrels, which are connected and disconnected by the rotation of the needle assembly within the barrel, being described, for example, in U.S. Pat. No. 4,507,i17, issued to Vining et al on Mar. 26, 1985; in U.S. Pat. No. 4,675,005, issued to DeLuccia on Jun. 23, 1987; in U.S. Pat. No. 4,747,830, issued to Gloyer et al on May 31, 65 1988; in U.S. Pat. No. 4,919,652, issued to Alter et al on Apr. 24, 1990; and in U.S. Pat. No. 4,986,813, issued to Blake III et al on Jan. 22, 1991. While DeLuccia, Alter, and Blake III teach the use of threaded screw connections, Vining and Gloyer uses quick release, quarter turn types of connection. Vining also describes means for providing the syringe, before use, with the needle retracted for safe handling. A disadvantage of these syringes is the additional requirement that the plunger must be twisted after an injection is given, before disposal of the syringe with the needle assembly in a retracted position. This twisting is needed to engage the needle assembly to the plunger assembly, and to disengage the needle assembly from the distal end of the barrel. However, this requirement places a burden on health care workers in an emergency situation, and can be expected to result in a failure to properly retract needles in some units before disposal.

Other devices of this in which the needle is loaded through the barrel interior include means for engaging the proximal end of the needle assembly with a mechanism extending from the distal end of the plunger assembly as the plunger mechanism reaches the distal end of its travel in dispensing medicine through the needle. Such devices are described, for example, in one of the embodiments of U.S. Pat. No. 4,675,005 to DeLuccia; in one of the embodiments of U.S. Pat. No. 4,692,156 to Haller; and in U.S. Pat. No. 4,804,370, issued to Haber et al on Feb. 14, 1989. In this Haber device, the needle extends outward through a small hole at the distal tip of the syringe barrel. The proximal end of the needle is provided with a flange, and the plunger assembly is provided with a needle capturing receptacle which engages this flange as the plunger assembly is moved to the distal end of the barrel, so that the needle is subsequently retracted into the barrel as the plunger assembly is withdrawn.

While such devices are operable without requiring the additional step of twisting the plunger after medicine is dispensed, they are still inconvenient to use, when compared to conventional syringes, because they do not accept conventional needle assemblies, and because, if it is necessary to install any type of needle assembly, the installation procedure is relatively complex and would violate the integrity of the sterility.

An important consideration in the design of a hypodermic syringe is the ability of the device to transmit axial forces to the needle from the barrel and plunger. Forces as high as several pounds may be required, both to insert the needle into the patient, and to withdraw the needle from the patient during the process of giving an injection. If the needle is to be retracted into the barrel of the syringe, means must be provided to prevent this retraction during the insertion of the needle into the patient, due to the necessary application of force to the needle as it is inserted.

In the devices having needle assemblies connected to the barrels with screw threads or quarter turn fasteners, to be disconnected by rotation of the plunger after the medication is dispensed, these fasteners prevent premature retraction of the needle. These devices are shown, for example, in U.S. Pat. Nos. 4,507,117, 4,675,005, 4,747,830, 4,919,652, and 4,986,813. While this method of holding the needle in place during injection is quite effective, the disadvantages of requiring the performance of the additional manual rotation step and nonstandard components remains.

In those devices having means for engaging the proximal end of the needle assembly with a mechanism extending from the distal end of the plunger assembly, the connection between the needle and the barrel must be strong enough to hold the needle in place as it is inserted into the patient. Further, the needle must subsequently be pulled directly out of this connection for retraction. Both of these actions are accomplished by applying an axial force to the needle. In the devices of U.S. Pat. No. 4,692,156 to Haller, the needle is mounted in an aperture within a deformable tapered mounting post, which deforms to slide through a passage in the barrel during retraction. In other devices, as shown, for example in U.S. Pat. Nos. 4,804,370 and 4,826,484 to Haber et al., the needle is retained by a tight fit within a distal hole of the barrel. This means that, for reliable operation, the force which must be applied for needle retraction, to overcome the attachment between the needle and the barrel, must be greater than the highest force expected during the insertion of the needle into the patient, together with a safety factor applied to cover variations in the process of manufacturing the syringe. If the needle is to be retracted during withdrawal from the patient, this force must be even higher. The requirement to apply such a large force places a significant burden on health care personnel and creates a potential danger to the patient.

The device described in U.S. Pat. No. 4,710,170 to Haber et al includes a needle carrier which is held in place within the barrel by means of a quick release fastener. After the dispensing of medication is completed, the plunger is manually rotated to release the carrier from engagement with the barrel. Thus, a requirement to perform an additional step is placed on health care personnel.

The device described in U.S. Pat. No. 4,790,822 to Haining includes a needle carrier which is held in place at the distal end of the barrel by opposing shoulders extending inward from the interior of the barrel. As the plunger is moved to the distal end of the barrel, a piston at the distal end of the plunger forces these shoulders apart, releasing the carrier to return with the plunger.

The patent literature also describes apparatus for causing the needle to be rotated transversely, about its attachment to the plunger as it is retracted into the barrel, to point toward a side of the barrel. This is done to prevent accidental or deliberate extension of the needle through the hole in the distal end of the barrel, by means of pushing the plunger inward. In other words, this feature provides further safety for health care and trash disposal workers, and goes another step toward preventing the subsequent use of the syringe by drug abusers. For example, U.S. Pat. No. 4,804,370, issued to Haber et al on Feb. 14, 1989, describes needle capturing receptacle with legs, for capturing a flange at the proximal end of the needle. Two of the legs are shorter than the others, so the needle is rotated transversely as it is retracted. As described in U.S. Pat. No. 4,986,813 to Blake III et al, a syringe includes a fitting fastening the needle assembly to the distal end of the plunger for retraction with a slot, extending inward from one side of the fitting, which is allowed to expand as the needle is fully retracted, throwing the needle out of alignment with the longitudinal axis of the plunger.

Blake III also describes the use of stopping surfaces extending into the barrel near its proximal end, angled to prevent removal of the plunger from the barrel, while allowing its assembly into the barrel as the syringe is fabricated. Such surfaces make it particularly difficult for a drug user to take the syringe apart to make it again operable or to retrieve the needle.

Thus, while the feature of needle retraction can be accomplished in a number of ways, the methods proposed in the prior art for providing this feature all have various disadvantages. What is needed is apparatus for providing needle retraction without substantially increasing the size or length of the syringe, as required when a separate needle carrier is employed, and without requiring the performance of an additional step, such as the rotation of the plunger, by health care personnel. Since health care facilities must carry a relatively large inventory of different sizes and types of syringes and needles, it is desirable that an improved syringe should accept the removal and attachment of needles in the standard way, from outside the distal end of the barrel. It is further desirable that the needle be releasibly held in place by positive means, such as a latch or movable abutting surface, rather than by reliance on a tight fit. Also, since conventional hypodermic syringes are low cost items used in large quantities by health care facilities, it is particularly desirable that the feature of needle retraction should be provided by a mechanism which is inherently simple and low in manufacturing cost. In particular, any improved syringe ideally will use existing syringe parts or slight modified parts so that existing mold tooling can be used.

SUMMARY OF THE INVENTION

In accordance with one aspect of the invention, there is provided a hypodermic syringe including a container for ejecting fluid having an internal cavity between a fluid ejecting end thereof and a proximal end thereof. The container also has a piston assembly having a seal end movable from the proximal end to the fluid ejecting end to eject fluid and retractable towards the proximal end. The syringe further includes a needle attachment assembly affixed to the fluid ejecting end of the container, the needle attachment assembly having a hollow first column with an opening extending therethrough in fluid communication with the cavity. The column is tapered inward at a distal end thereof and has a plurality of slits from the distal end thereof towards the container separating a plurality of segments at the distal end. In addition, the syringe includes a needle subassembly, including a needle with hole extending axially there-through, and a needle flange affixed remote from one end of the needle. A second hollow column extends from the flange towards the one end and is sized to fit within the first column opening such that the end of the segments are juxtaposed to one surface of the flange. The needle subassembly further includes means juxtaposed to the other side of the flange for holding the needle subassembly on the attachment assembly column. Finally, the syringe includes needle extractor means, including a third hollow column affixed to the seal end of the piston assembly. The third column is sized such that the exterior thereof enters the first column and separates the segments so that the ends thereof are spaced from the one surface of the flange. The third column further is sized such that the interior thereof grabs the second column and the needle assembly, including the flange is retracted through the first column upon retraction of the piston assembly.

BRIEF DESCRIPTION OF THE DRAWINGS

Preferred embodiments of the subject invention are hereafter described with specific reference being made to the following Figures, in which.

DETAILED DESCRIPTION

Figure 1:
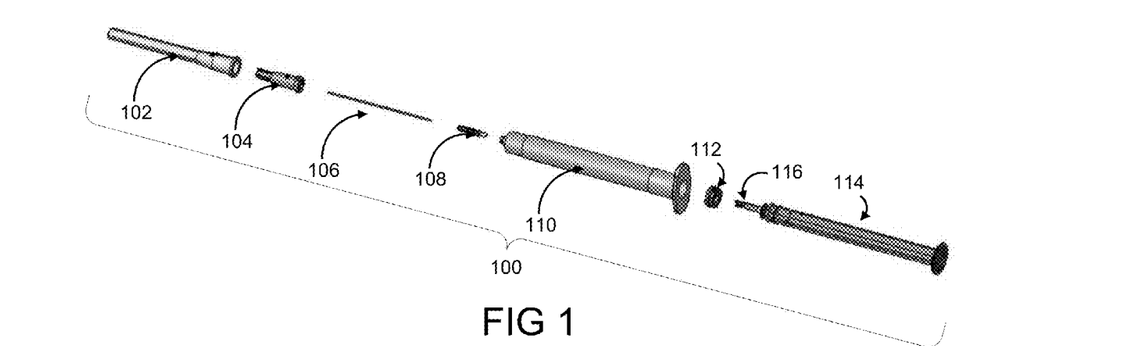
FIG. 1 depicts another embodiment of a hypodermic syringe.

FIG. 1 depicts another embodiment of a hypodermic syringe 100. The hypodermic syringe 100 includes a needle cover 102, a Luer nut 104, a needle 106, a needle collar 108, a barrel 110, a piston 112, a plunger 114 and an extractor 116. In one embodiment, the needle 106 is inserted and held by the needle collar 108. The needle collar 108 is then inserted into the Luer nut 104 which connects to the barrel 110. The piston 112 connects to one end of the plunger 114 before the plunger 114 is inserted into the barrel 110.

Figure 2:
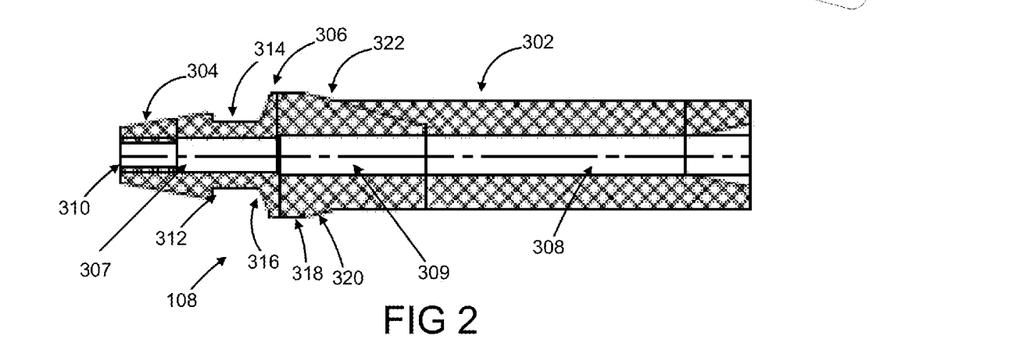
FIG. 2 depicts one embodiment of a needle collar.

FIG. 2 depicts one embodiment of the needle collar 108. The needle collar 108 is mostly cylindrical in shape and includes an upper portion 302, a lower portion 304, a neck portion 306 which separates the lower portion 304 from the upper portion 302 and a central channel 308 extending through the upper portion 302, the neck 306 and at least midway through the lower portion 304. The central channel 308 includes a first portion 307 that is sized to engage and hold the needle 106 and a second portion 309 that has a larger diameter than the first portion 307 to accommodate an adhesive for securing the needing in the central channel 308. The upper portion 304 includes a first side 310 and a second side 312 with the first side 310 being narrower in cross sectional width than the second side 312 such that the lower portion 304 tapers from the second side 312 towards the first side 310. The neck portion 306 is positioned at the end of the upper portion 302 closest to the lower portion 304 and the neck portion 306 connects to the lower portion 304 by a shaft 314. The neck portion 306 has a cross sectional width that is wider than the widths of each of the upper portion 302 and the lower portion 304. The neck portion 306 has an lower end 316, a central portion 318 and an upper end 320. The central portion 318 tapers towards the lower end 316 where it meets the shaft 314 and the central portion 318 includes a tapered section 320 that tapers towards the upper end 322 where it meets the upper portion 302. The shaft 314 is connected to the second side 312 of the lower portion 304 of the needle collar 108.

Figure 3:
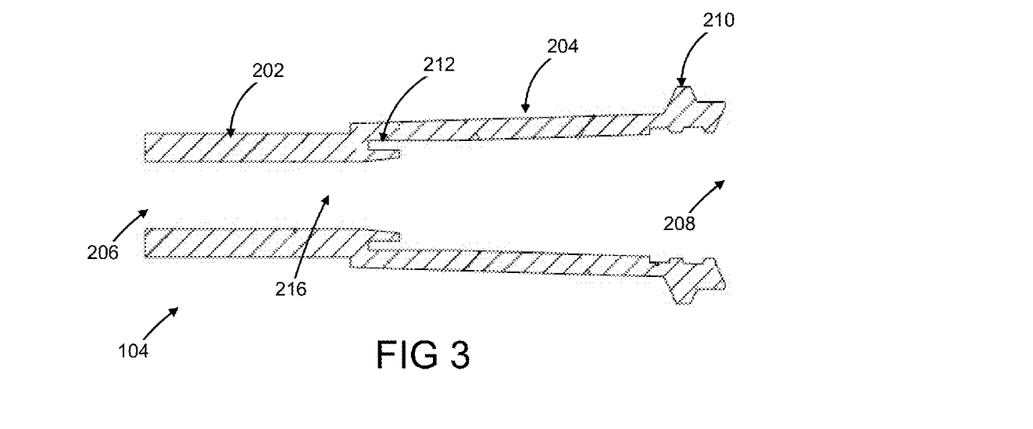
FIG. 3 depicts one embodiment of a Luer nut used in a hypodermic syringe.

FIG. 3 depicts one embodiment of a Luer nut 104 used in a hypodermic syringe 100. Consistent with this embodiment, the needle 106 is coupled to the needle collar 108 which is inserted into the Luer nut 104. The Luer nut 104 has a substantially cylindrical shape and includes an upper portion 202 and a lower portion 204 with a first opening 206 on the upper portion 202 and a second opening 208 on the lower portion 204. The first opening 206 is sized to accommodate the needle collar 108. The needle collar 108 is held in the Luer nut 104 by the flexible seal 212. A central channel 216 extends through the Luer nut 104 with the central channel 216 having a larger cross sectional width in the lower portion 204 than in the upper portion 202. In one embodiment, the Luer nut 104 includes a threaded portion 210 that is coupled to a corresponding threaded portion of the barrel 110. In another embodiment, the Luer nut 104 is a Luer slip which slips onto the end of the barrel 111 and is held in place by friction.

The flexible seal 212 is created at an interconnection of the upper portion 202 with the lower portion 204. The flexible seal 212 is configured to create a seal between the Luer nut 104 and the needle collar 108 such that fluid in the barrel does not escape when transferred from the barrel 110 to the needle 106. When the needle collar 108 engages the flexible seal 212, the flexible seal 212 expands to create a seal with the tapered section 320 of the neck portion 306 of the needle collar 108 the lower portion 302 of which is inserted into the second opening 208.

Figure 4:
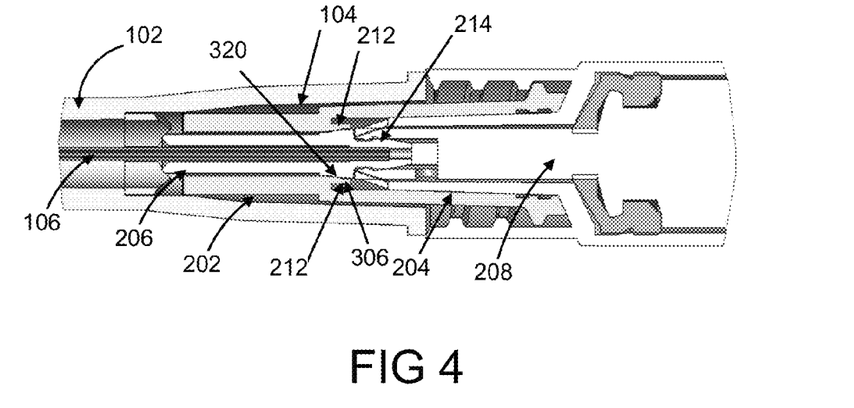
FIG. 4 depicts one embodiment of a Luer nut engaging a barrel, a needle collar and the needle.

FIG. 4 depicts one embodiment of the Luer nut 104 engaging the barrel 110, the needle collar 108, the needle 106 and the needle cover 102. Consistent with this embodiment, the tapered section 320 of the neck portion 306 of the needle collar 108 engages the flexible seal 212 of the Luer nut 104 preventing the needle collar 108 from disengaging the Luer nut 104. To engage the needle collar 108 with the flexible seal 212, the needle collar 108 is inserted into the second opening 208 of the Luer nut 104 and moved towards the first opening 206. As the neck portion 306 of the needle collar 108 moves past the flexible seal 212, the flexible seal 212 is pushed away from the needle collar 108 until the sides of the neck portion 306 engage the flexible seal 212 preventing the needle collar 108 from moving further into the Luer nut 104. Further, in this position, the flexible seal 212 is in contact with the sides of the neck portion 306 in such a manner as to create a seal between the flexible seal 212 and the neck portion 306 preventing liquid or air from passing through the seal.

Figure 5:
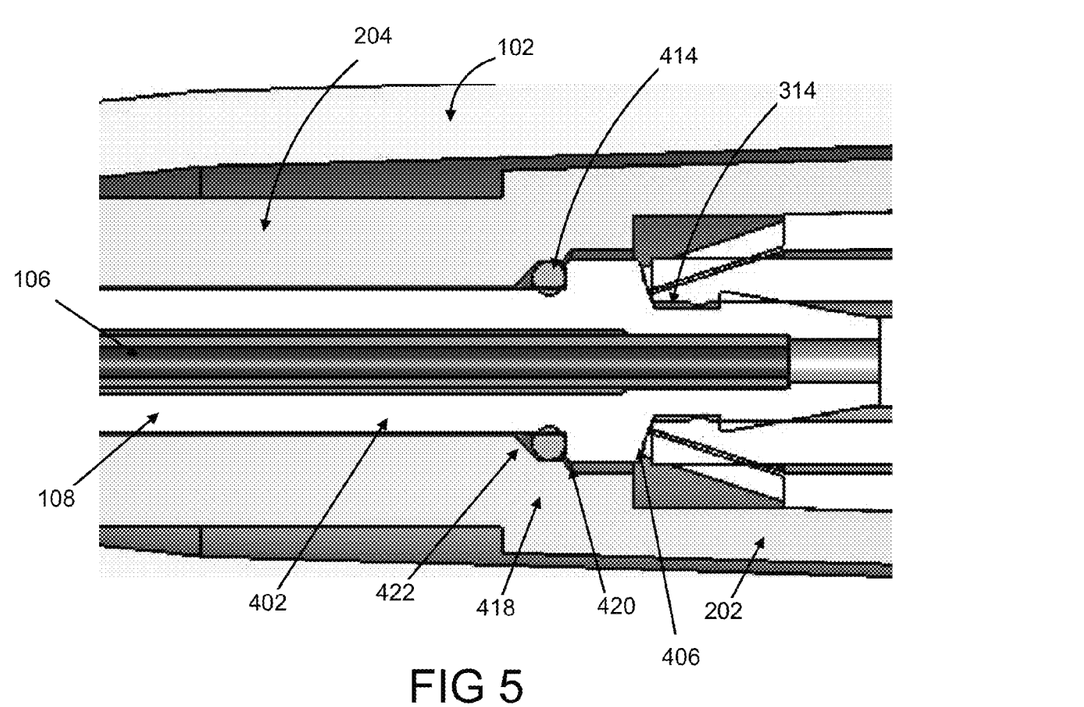
FIG. 5 depicts another embodiment of a Luer nut and a needle collar.

FIG. 5 depicts another embodiment of a Luer Nut 104 and a needle collar 108. Consistent with this embodiment, the flexible seal 212 is replaced by a ring 414 made of a material having memory characteristics. In one embodiment, the ring is an O-ring. The neck portion 406 of the needle collar 408 tapers towards the shaft 314, but does not taper towards the upper portion 402. The ring 414 engages the neck portion 406 of the needle collar 408 where the neck portion 406 meets the upper portion 402. In addition, the flexible seal 212 of the Luer nut 104 is replaced with an opening 418 in the inner portion of the Luer nut 104 where the lower portion 202 meets the upper portion 204. The opening 418 includes two ledges with the first ledge 420 positioned between the upper portion 204 and the lower portion 202 of the Luer nut 104. The first ledge 420 is sized such that the upper portion 402 of the needle collar 408 does not engage the first ledge 420, but a portion of the neck 406 of the needle collar 408 engages the first ledge 420. The second ledge 422 is sized to accommodate the ring 414 such that the neck 406 of the needle collar 408 compresses the ring 414 into the second ledge 422.

In one embodiment, the upper portion of the first ledge 420 tapers towards the lower portion of the second ledge 422 and the upper portion of the second ledge 422 tapers towards the upper portion 204 of the Luer nut 104. Consistent with this embodiment, the ring 414 rests on the second ledge 422. As the needle collar 108 moves from the second opening 208 of the Luer nut 104 towards the first opening 206 of the Luer nut 104, the neck portion 406 of the needle collar 408 engages the ring 414 forcing the ring 414 upward towards the upper portion of the second ledge 422. In addition, the ring 416 is sized such that the ring 416 protrudes into the path of the needle collar 408 which causes the upper portion 402 of the needle collar 408 to press against the ring 414 creating a seal between the ring 414 and the second ledge 422 and also holding the needle collar 408 in the Luer nut 104.

Figure 6:
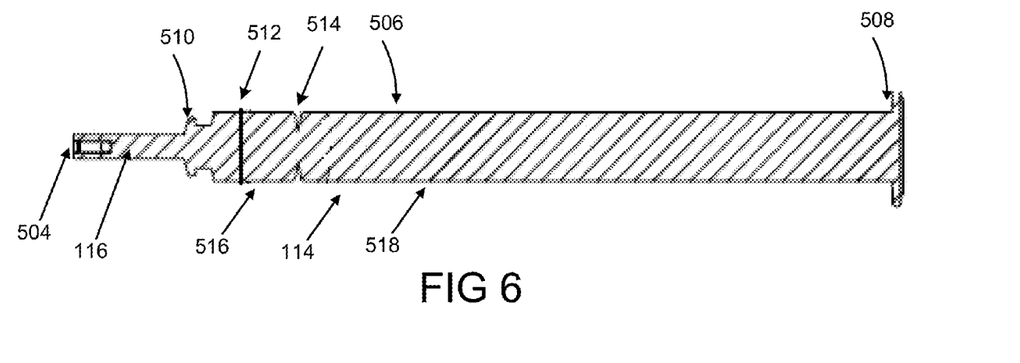
FIG. 6 depicts one embodiment of a plunger.

FIG. 6 depicts one embodiment of the plunger 114. The plunger 114 includes the extractor unit 116 positioned at one end of the plunger 114, an elongated slide 506 and a gripping unit 508. The extractor unit 116 includes an opening 504 configured to engage the upper portion 304 of the needle collar 108 of FIG. 1 when the needle collar 108 is coupled to the barrel 110 by the Luer nut 104. In one embodiment, the extractor unit 116 tapers towards the opening 504. The opening 504 has a cross sectional width that is wider than the cross sectional width of the first side 310 of the lower portion 304 of the needle collar 108 and smaller than the second side 312 of the lower portion 304. A force is applied to the plunger 114 which pushes the extractor unit 116 towards the Luer nut 104 holding the needle collar 108 such that the opening 504 engages lower portion 304 of the needle collar 108. When the plunger 114 is pulled away from the Luer nut 104, the needle 106 is pulled into the barrel 110 by the extractor unit 116.

The force required to disengage the extractor unit 116 from the needle collar 108 should be greater than the force required to remove the needle collar 108 from the Luer nut 104. In one embodiment, the force required to disengage the extractor unit 116 from the needle collar 108 is at least twice the amount of force required to pull the needle collar 108 from the Luer nut 104. In another embodiment, the force required to disengage the extractor unit 116 from the needle collar 108 is 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 165%, 175%, 180%, 185%, 190% or more than 190% greater than the amount of force required to pull the needle collar 108 from the Luer nut 104. In one embodiment, the force required to push the extractor unit 116 over the needle collar 108 is approximately 650 grams. In an additional embodiment, the force required to remove the needle collar 108 from the extractor unit 116 is at least 500 grams and the force required to remove the needle collar 108 from the Luer nut 104 is at least 50 grams. In an additional embodiment, the force required to push the extractor unit 116 over the needle collar 108 is 525 grams, 530 grams, 535 grams, 540 grams, 545 grams, 550 grams, 555 grams, 560 grams, 565 grams, 570 grams, 575 grams, 580 grams, 585 grams, 590 grams, 595 grams, 600 grams, 605 grams, 610 grams, 615 grams, 620 grams, 625 grams, 630 grams, 635 grams, 640 grams, 645 grams or any other force capable of pushing the extractor unit 116 over the needle collar 108, and the force required to remove the needle collar 108 from the Luer nut 104 is 55 grams, 60 grams, 65 grams, 70 grams, 75 grams, 80 grams, 85 grams, 90 grams, 95 grams, 100 grams, 105 grams, 110 grams, 115 grams, 120 grams, 125 grams, 130 grams, 135 grams, 140 grams, 145 grams, 150 grams, 155 grams, 160 grams, 165 grams, 170 grams, 175 grams or any other force capable of removing the needle collar 108 from the Luer nut 104 without disengaging the extractor unit 116 from the needle collar 108. This guarantees that the extractor unit 116 will not pull off the needle collar 108 after actuation as the plunger 114 is pulled back. In another embodiment, the force required to pull the needle out of the needle collar is at least 5 Kg.

Figure 7A:
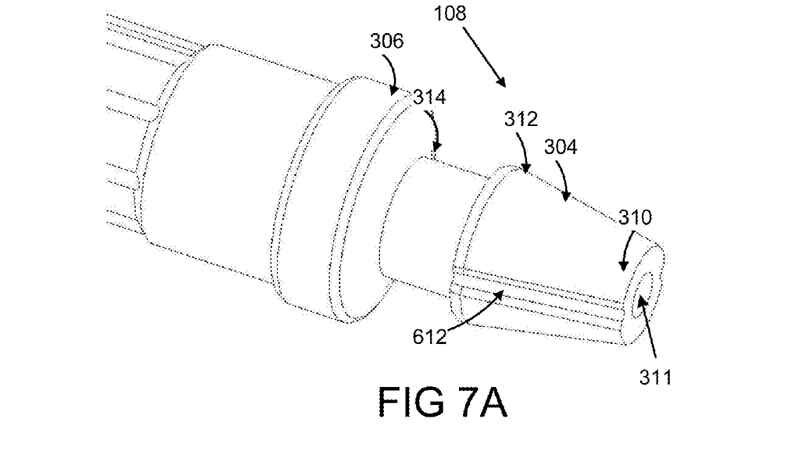
FIG. 7A depicts one embodiment of the needle collar.

FIG. 7A depicts one embodiment of the needle collar 108. Consistent with this embodiment, the lower portion 304 of the needle collar 108 includes at least one groove 612 or depression formed longitudinally in the lower portion 304 of the needle collar 108. In one embodiment, the groove 612 extends along one portion of the lower portion 304 such that a channel is formed through the lower portion 304. In another embodiment, two or more grooves 612 are longitudinally formed in the lower portion 304 of the needle collar 108. In another embodiment, the groove 612 acts to prevent the plunger 114 from becoming hydraulically locked in the barrel 110 by providing a path for fluid to flow from the area between the shaft 314 and the extractor unit 116, down groove 612 and into the needle through opening 311 when the needle collar 108 is engaged by the extractor unit 116.

Figure 7B:
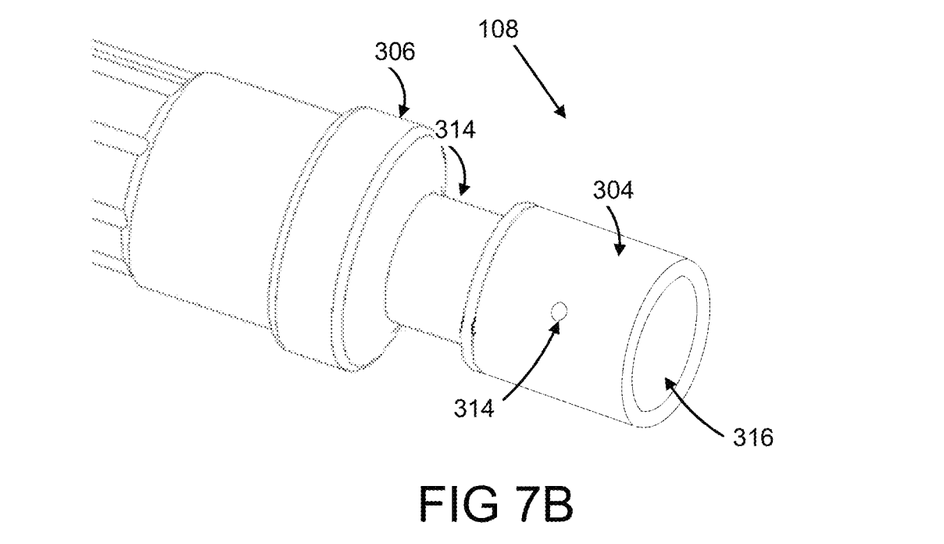
FIG. 7B depicts another embodiment of a needle collar.

FIG. 7B depicts another embodiment of the needle collar 108. Consistent with this embodiment, the lower portion 304 of the needle collar 108 is substantially cylindrical in shape and includes a channel 316 extending the length of lower portion 304 and connecting to and allowing liquid to flow through the needle. The channel 316 is sized to accommodate the extractor unit 116 such that the extractor unit 116 extends into the opening and the sides of the extractor unit 116 are in contact with the sides of the channel 316. In one embodiment, the channel 316 is sized such that the extractor unit 116 is secured in the channel 316 by friction. Consistent with this embodiment, the amount of force required to remove the extractor unit 116 from the channel 316 is approximately twice the force required to insert the extractor unit 116 into the channel 316. In another embodiment, the interior surface of the lower portion 304 includes a plurality of ridges which engage corresponding ridges on the surface of the extractor unit 116 to secure the extractor unit 116 in the channel 316. Consistent with this embodiment, the amount of force required to remove the extractor unit 116 from the channel 316 is approximately twice the force required to remove the extractor unit 116 from the channel 316. In another embodiment, the lower portion 304 includes at least one hole 314 that extends to the channel 316 preventing the extractor unit 116 from being hydraulically locked from entering the channel 316. In one embodiment the extractor unit 116 is shaped like the lower portion 304 shown in FIG. 7A, including the groove 612, to allow for the extractor unit 116 and the lower portion to effectively and more easily mate.

Figure 8:
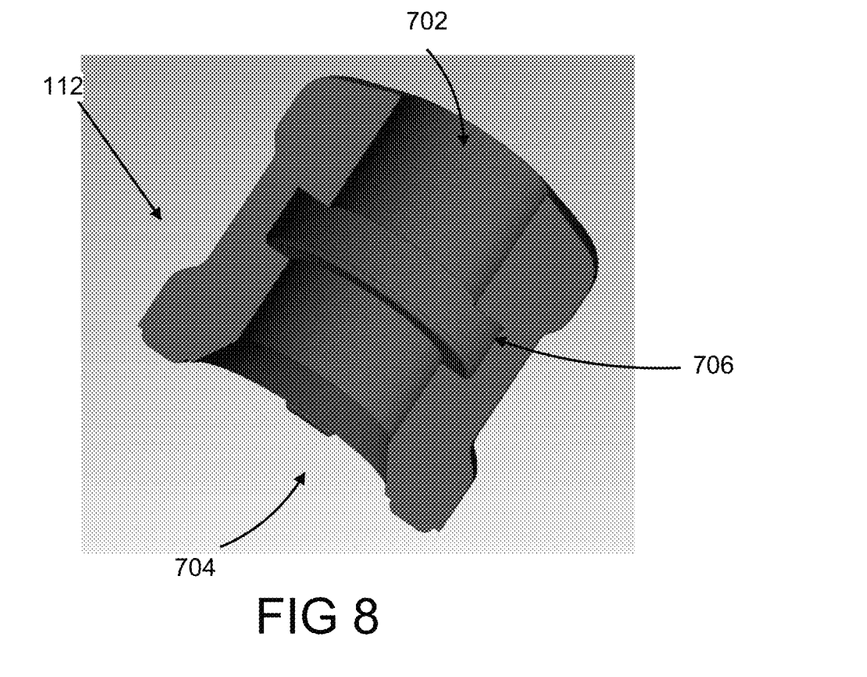
FIG. 8 depicts a cross section of one embodiment of a piston.

FIG. 8 depicts a cross section of one embodiment of the piston 112. The piston 112 is made from a material having memory characteristics such as, for example, natural rubber, synthetic rubber and latex free rubber. The material may also include silicone, polyethylene, plastic or any other malleable material having memory characteristics. The piston 112 includes a first opening 702, a second opening 704 and a ridge 706 on the inner surface of the piston 112 between the first opening 702 and the second opening 704. In one embodiment, the first opening 702 and second opening 704 are sized such that the cross sectional width of the first opening 702 and second opening 704 are substantially identical to the cross sectional width of the extractor unit 116. The piston 112 is slid over the extractor unit 116 such that the ridge 706 engages the flange 510 on the plunger positioned between the extractor unit 116 and the elongated slider 506 (as depicted in FIG. 6) such that the piston 112 is securely coupled to the plunger 114. The plunger 114 is sized such that the plunger 114 slides into the barrel 110 with the sides of the elongated slider 506 and the piston 112 contacting the inner sides of the barrel 110. In one embodiment, the end of the piston 112 closest to the needle 106 is tapered towards the needle 106. By tapering the piston 112, the force required to move the piston is reduced. In another embodiment, the extractor unit 116 is tapered such that the end of the extractor unit 116 closest to the plunger 114 has a larger cross sectional width than the portion of the extractor unit 116 closest to the opening 702.

Figure 9A:
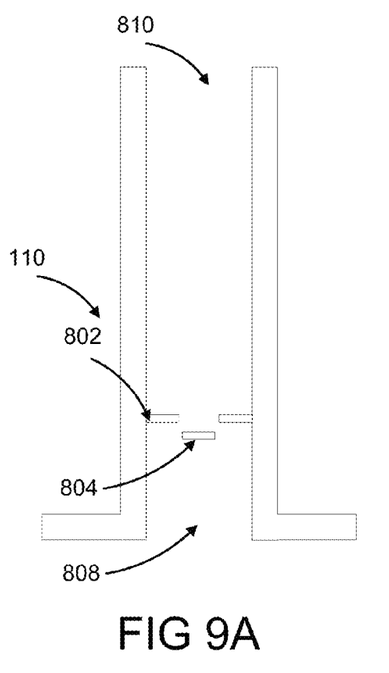
FIGS. 9A and 9B depict one embodiment of bumps on an inner surface of a barrel.

FIG. 9A depicts one embodiment of a cross section of the inner surface of the barrel 110. Consistent with this embodiment, the inner surface of the barrel 110 includes a first opening 808 and a second opening 810 and a first row of bumps 802 arranged circumferentially around the inner surface of the barrel 110 with a gap between each of the bumps. In one embodiment, a second row of bumps 804 is arranged on the side of the first row of bumps 802 closest to the first opening 808. Consistent with this embodiment, each of the bumps in the second row 804 is arranged such that they align with the gap between the bumps in the first row of bumps 802. In one embodiment, each row includes three to four bumps. In another embodiment each row includes more than four bumps. In yet another embodiment one row includes at least three bumps and the other row includes more than three bumps.

The rows of bumps 802 and 804 are configured such that the stop disc 512 disposed between the piston 112 and notch 514 (as shown in FIG. 6) is able to move over the first row of bumps 802 in a direction away from the second opening 810, but are only able to move over the second row of bumps 804 in a direction away from the second opening 810 with the use of a large amount of force. In one embodiment, the notch 514 separates the piston 112 into an upper portion 516 and a lower portion 518. Consistent with this embodiment, the depth of the notch 514 is sufficient to allow the piston to be separated into two pieces comprising the upper portion 516 and the lower portion 518 of the piston 112 when the piston 112 is bent at the notch 514. This can be more easily facilitated when the stop disc 512 engages the second row of bumps 804. At that position, the piston 112 may be bent using the barrel 110 to provide leverage. With sufficient bending force, the piston can be separated into two portions with the upper portion 516 remaining inserted in the barrel 110 and the lower portion 518 remaining exterior to the barrel 110. In one embodiment, the notch 514 is continuously formed around the circumference of the piston 112. In another embodiment, the notch 514 is formed from a plurality of individual notches made around the circumference of the piston 112.

In another embodiment, the height of the bumps 802 and 804 are set such that the piston 112 cannot move back towards the needle 102 once the piston is pulled over the bumps 802 or 804 or can only be moved back with a large amount of force In one embodiment, the portion of the bumps 802 and 804 nearest to the first opening 808 rise to a higher level above the inner surface of the barrel 110 than the portion of the bumps 802 and 804 furthest from the first opening 808. In another embodiment, the bumps 802 and 804 taper from the higher point to the lower point. In another embodiment, the first row of bumps 802 are lower than the second row of bumps 804. In one embodiment, the force required to pull the piston 112 over the first row of bumps 802 is 1.2-1.6 Kg. In another embodiment, the force to pull the piston 112 over the second row of bumps 804 is at least 5 Kg.

Figure 9B:
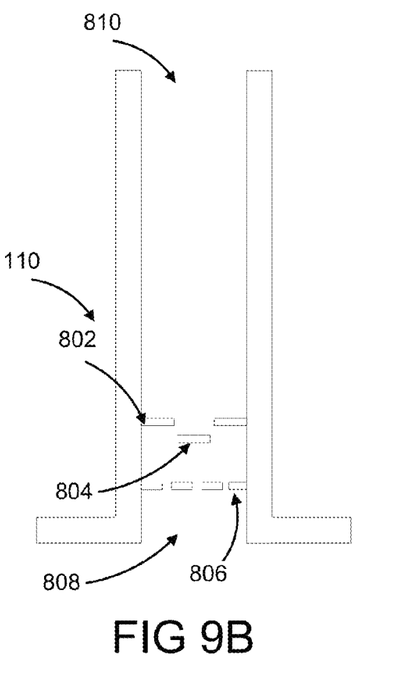

FIG. 9B depicts another embodiment of the barrel 110 that includes a first row of bumps 802 along the inner wall of the barrel 110, a third row of bumps 806 and a second row of bumps 804 arranged between the first row of bumps 802 and the third row of bumps 806. Consistent with this embodiment, the bumps 806 in the third row are raised higher above the inner surface of the barrel 110 than the second row of bumps 804 and the second row of bumps are raised higher than the bumps 802 in the first row. In another embodiment, the bumps 806 in the third row are raised above the inner surface of the barrel 110 such that the piston assembly is prevented from passing over the bumps 806.

Figure 10A:
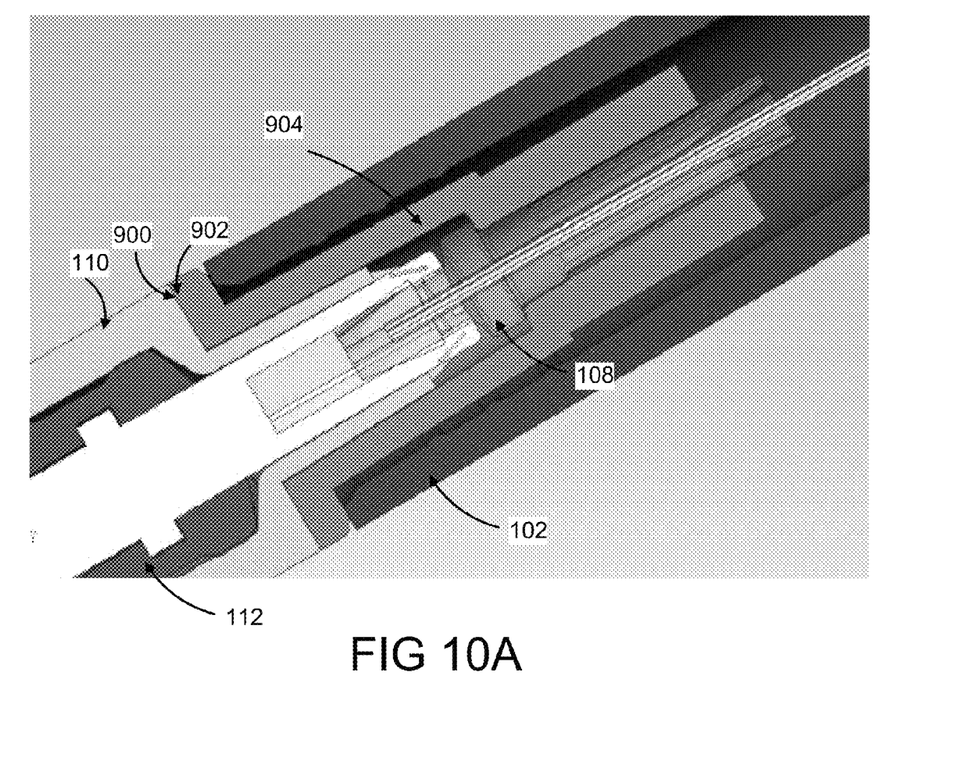
FIG. 10A depicts one embodiment of a syringe.

FIG. 10A depicts one embodiment of a syringe. Consistent with this embodiment, the barrel 110 includes a rim 900 which engages a flange 902 on a fitting in the form of a securing cap 904. In one embodiment, the rim 900 of the barrel 110 and the flange 902 of the securing cap 904 are welded together. In another embodiment, the rim 900 and the flange 902 are secured together by an adhesive. In yet another embodiment, the rim 900 and the flange 902 are secured using a pressure fit. In a further embodiment, as shown in FIG. 10B, the rim 900 and the flange 902 are secured using offset ridges or locking ridges 908 on the exterior of the tip of the barrel 110 and corresponding offset ridges or locking ridges 910 on the interior of the securing cap 904.

Figure 10B:
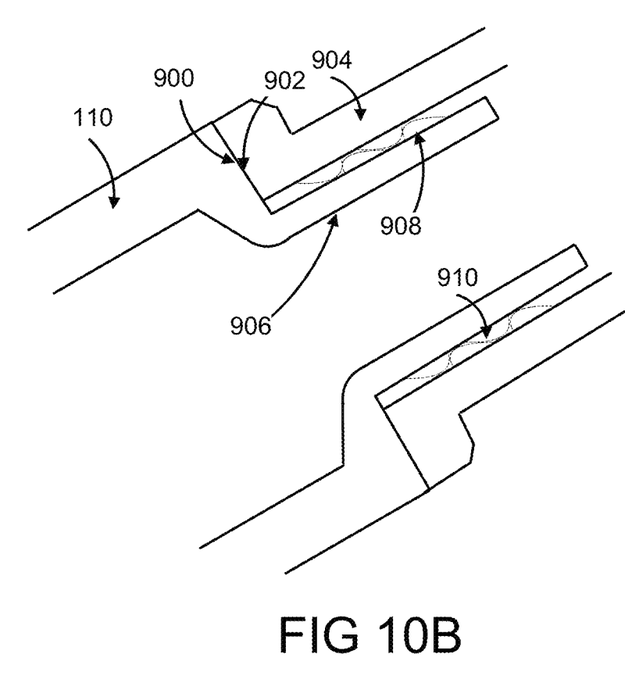
FIG. 10B depicts another embodiment of a syringe.

FIG. 10B depicts one embodiment of a securing cap 904 engaging a barrel 110. Consistent with this embodiment, the tip of the barrel 906 includes one or more ridges 908 arranged around the external surface of the barrel tip 906. The ridges 908 taper away from the rim 900 such that the portion of each ridge 908 closest to the rim 900 extends further from the surface of the barrel tip 906 than the portion of the ridge 908 furthest from the rim 900. The securing cap 904 includes corresponding ridges 910 which are arranged on the inner surface of the securing cap 904. The securing cap 904 ridges taper towards the flange 902 such that the portion of each ridge farthest from the flange 904 extends further from the inner surface of the securing cap 904 than the portion of each ridge 910 closer to the flange 904. The ridges 908 are arranged on the barrel tip 906 and the ridges 910 are arranged on the securing cap 904 such that the ridges 910 are positioned between the ridges 908 when the rim 900 is in contact with the flange 902 with the high points of the ridges 908 and 910 contacting each other thereby securing the securing cap 904 to the rim 900.

In one embodiment, the syringe is a 1 cc syringe used with an intravenous needle system. In another embodiment, the syringe is marked with an insulin scale. In yet another embodiment, the syringe is a ½ cc syringe. In one embodiment, the piston 112 and/or the inside of the barrel 110 are treated with a silicone lubricant to provide for smooth motion relating to the movement of the plunger 114 through the barrel 110.

Figure 11:
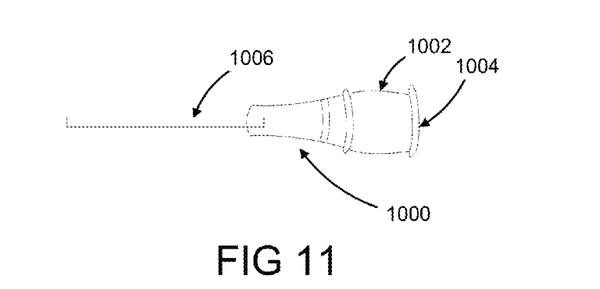
FIG. 11 depicts one embodiment of a catheter Luer fitting.

FIG. 11 depicts one embodiment of a catheter 1000. The catheter 1000 includes a catheter fitting 1002 having an opening 1004 at one end of the catheter fitting 1002 and a plastic tube 1006 at the opposing end of the catheter fitting 1002. In one embodiment, the opening 1004 is sized to accommodate the upper portion 202 of a Luer nut 104 (as shown in FIG. 3) or the upper portion 910 of the securing nut 904 (as shown in FIG. 10A) and the plastic tube 1006 is sized to accommodate a needle 106. Consistent with this embodiment, the Luer nut 104 engages the catheter fitting 1002 allowing the needle 106 to enter into the plastic tube 1006. The length of the plastic tube 1006 is sized such that the end of the needle 106 extends beyond the end of the plastic tube 1006 allowing the needle to pierce the skin of a patient before the plastic tube 1006 is inserted into the patient and to also allow extraction of the needle 106 from the plastic tube 1006 after the plastic tube 1006 is inserted below the patient's skin.

Figure 12:
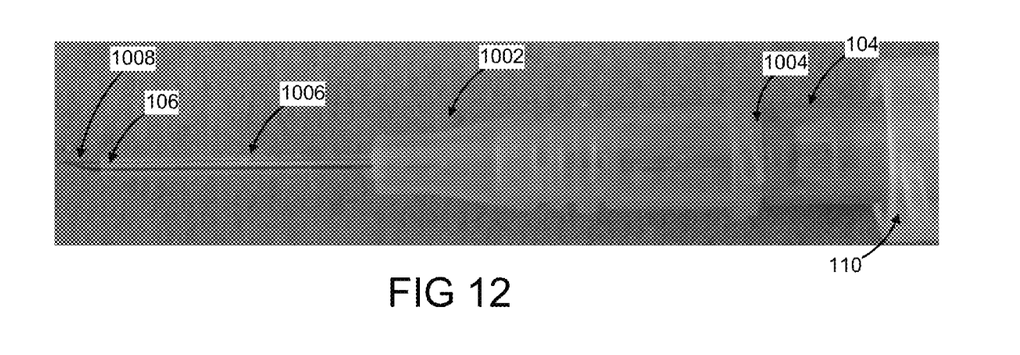
FIG. 12 depicts one embodiment of a catheter Luer fitting engaging a Luer nut.

FIG. 12 depicts one embodiment of the catheter fitting 1002 engaging a Luer nut 104. Consistent with this embodiment, the upper portion 202 of the Luer nut 104, which is coupled to the barrel 110, is inserted into the opening 1004 of the catheter fitting 1002. In addition, the needle 106 extends through the plastic tube 1006 to a point beyond the end of the plastic tube 1006 to expose the sharpened end of the needle 1008. Accordingly, to insert the catheter 1000, the needle 106 first pierces the skin of the patent allowing the tube 1006 to be inserted into the patient. In one embodiment, the catheter fitting 1002 is configured to accommodate an intravenous connector which allows an IV bag to be coupled to the catheter fitting 1002.

Retraction of the needle may be accomplished in the same manner as retraction of the needle described above. However, upon retraction of the needle, the plastic tube will remain intact in the patient. After retraction of the needle, the catheter fitting 1002 may be disengaged from the Luer nut 104 to allow the catheter fitting 1002 to be coupled to an IV bag or another object.

Figure 13A:
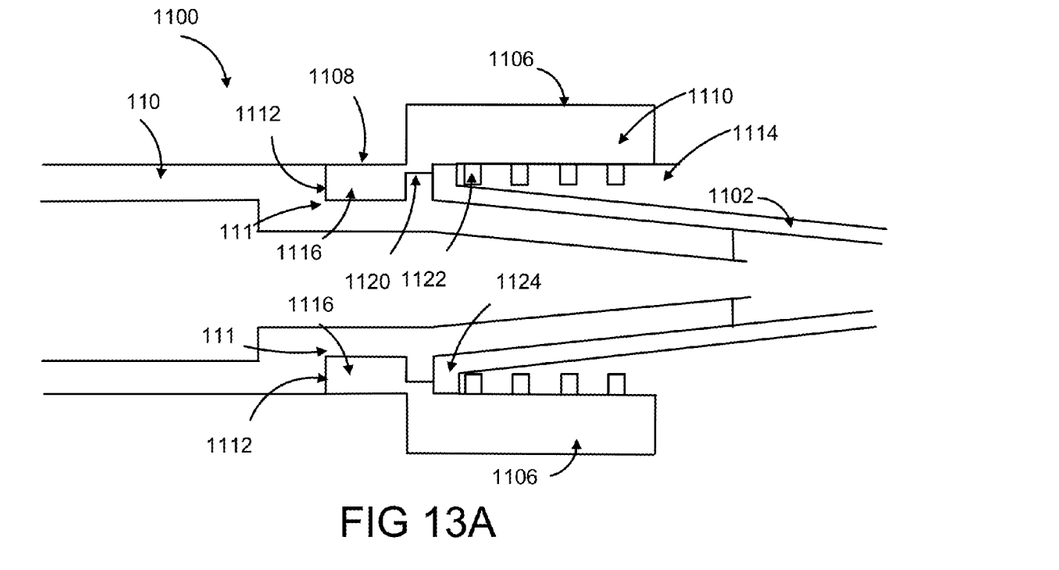
FIG. 13A depicts one embodiment of a syringe with a Luer nut attached to the syringe.
Figure 13B:
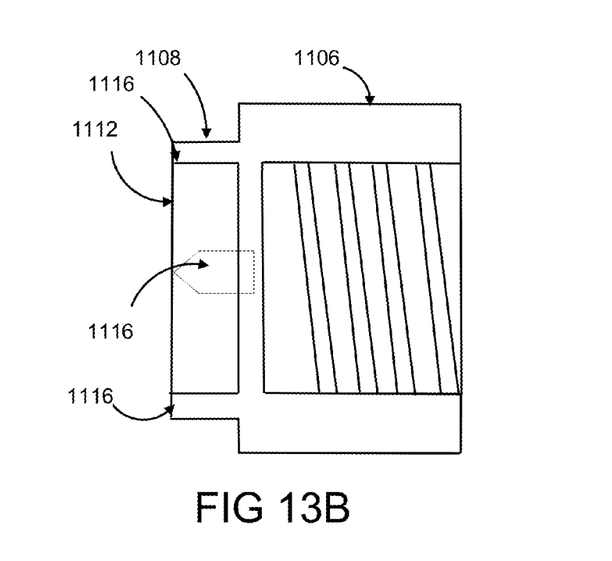
FIG. 13B depicts of a top view of one embodiment of the collar.
Figure 13C:
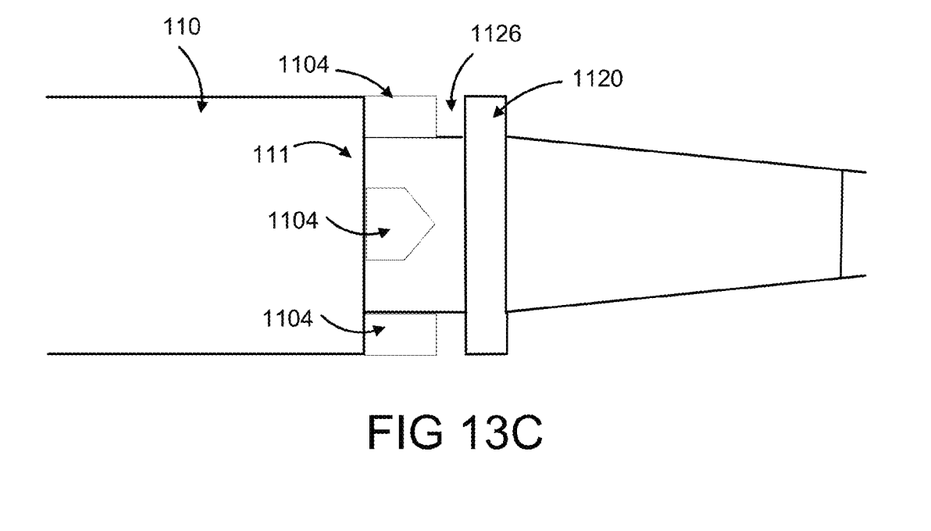
FIG. 13C depicts one embodiment of the end of the barrel.
Figure 13D:
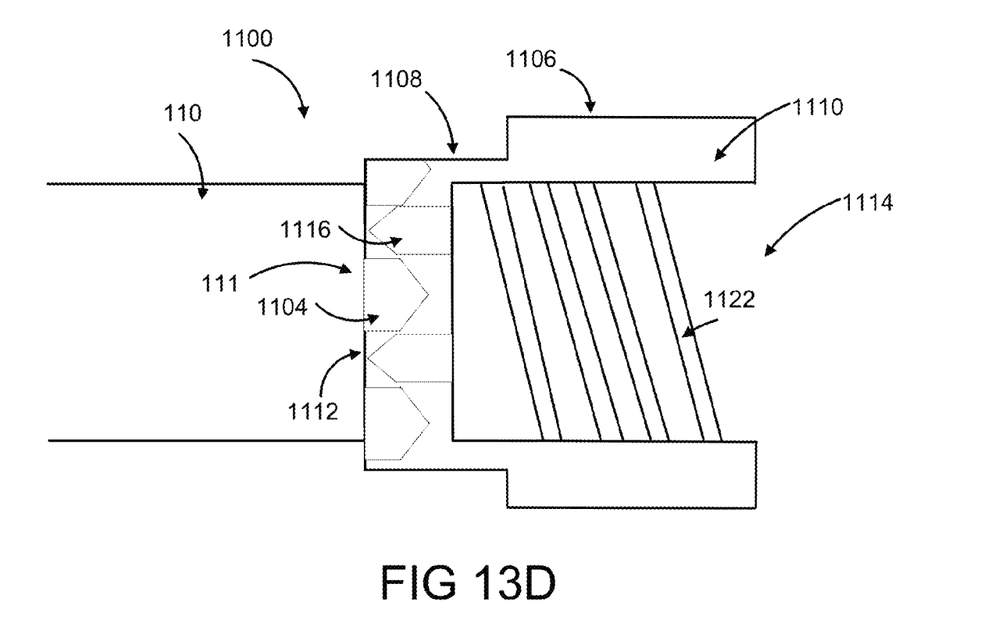
FIG. 13D depicts one embodiment of the collar engaging the end of the barrel.

FIGS. 13A through 13C depict one embodiment of a syringe 1100 with a Luer nut 1102 attached to a barrel 110 of the syringe 1100. Consistent with this embodiment, the end of the barrel 111 closest to the needle collar 108 (not shown) includes a plurality of extensions 1104 approximately evenly spaced around the periphery. A removable collar 1106 includes a lower portion 1108, an upper portion 1110, a flat bottom portion 1112 and an open upper portion 1114. The lower portion 1108 is formed with a plurality of notches 1116 located on the inside of the lower portion 1108 that are each designed to engage a corresponding extension 1104 at the bottom portion of the end of the barrel 111. The engagement of the extensions 1104 with the notches 1116 prevents the removable collar 1106 from rotating around the center axis of the barrel 110 as shown in FIG. 13D below.

The barrel 110 includes a ridge 1120 adjacent to the lower portion of the end of the barrel 111 which is configured to engage a portion of the notches 1116 on the removable collar 1106 when the notches 1116 are engaged with the extensions 1104 on the end of the barrel 111. Each notch 1116 rises above an inner surface of the lower portion 1108 of the collar 1106 such that a portion of each notch 1116 closest to the upper portion 1110 of the removable collar 1106 engages the ridge 1120 on the end of the barrel 111. The ridge 1120 is of sufficient height to secure the notches 1116 and the collar 1106 to the barrel 110 as discussed in FIG. 13B below.

The inside of the upper portion 1110 of the removable collar 1106 includes a spiral groove 1122 that correspond to ridges 1124 on the lower end of the Luer Nut 1102. In one embodiment, the ridges 1124 are formed around the entire circumference of the lower portion of the Luer Nut 1102. In another embodiment, the ridges 1124 are formed around a portion of the circumference of the lower portion of the Luer nut 1102. In another embodiment, the Luer nut 1102 includes two tabs extending from the lower portion of the Luer nut 1102 on opposing sides. In one embodiment, the spiral grooves 1122 on the inner surface of the upper portion 1110 of the removable collar 1106 are angled in relation to the bottom of the Luer nut 1102. In another embodiment, the spiral grooves 1122 have an upper portion which taper away from the collar 1106 such that the ridges 1124 are pushed over the spiral grooves 1122 in a direction towards the barrel 110, but cannot be pushed over the grooves in a direction away from the barrel 110. In another embodiment, a Luer slip is used where the Luer slip is held in place on the barrel by pressure and/or friction. The grooves may be other than spiral depending on the design of the Luer nut 1102.

FIG. 13B depicts a top view of one embodiment of the collar 1106. Consistent with this embodiment, a plurality of notches 1116 extend around the periphery of the inside of the lower portion 1108 of the collar 1106. The notches 1116 have a rectangular or square base that extends from about the lower third of the upper portion 1110 towards the flat bottom portion 1112 with the end of each notch 1116 that is closest to the flat bottom portion 1112 converging to a point. In addition, the base extends above the inside surface of the lower portion 1108 such that a portion of the base closest to the upper portion 1110 engages the ridge 1120 on the tip of the barrel 110 to prevent the collar 1106 from disengaging the barrel 110. In one embodiment, the collar 1106 includes four notches 1116 that are approximately equally spaced and separated from each other by four separating gaps with the separating gaps being sized to accommodate the extensions 1104 on the end of the barrel 111.

FIG. 13C depicts one embodiment of the end of the barrel 111. Consistent with this embodiment, a plurality of extensions 1104 are arranged around the periphery of the end of the barrel 111 with the bottom surface of each extension 1104 being substantially flush with the top surface of the barrel 110. The extensions 1104 have a rectangular or square base that extend from the top of the barrel 110 at ridge 1120 towards the upper portion of the end of the barrel 111 with the end of each extension 1104 converging to a point. The number of extensions 1104 on the barrel 110 is equal to the number of notches 1116 on the collar 1106. Further the extensions 1104 are substantially equally spaced from each other and are separated by gaps. The extensions 1104 are sized to engage the gaps between the notches 1116 on the collar 1106. In addition, the gaps between the extensions 1104 are sized to engage the notches 1116 on the collar. The ridge 1120 is positioned on the barrel tip such that the pointed ends of the notches 1116 contact the ledge of the barrel 110 while the end of each notch 1116 opposite the pointed end engages the ridge 1120.

FIG. 13D depicts one embodiment of the collar 1106 engaging the end of the barrel 111. Consistent with this embodiment, the notches 1116 are pushed over the ridge 1120 such that the non pointed end of each notch 1116 is in contact with the bottom of the ridge 1120 preventing the collar 1106 from disengaging the barrel 110. In addition, the extensions 1104 engage the gaps between the notches 1116 and the notches 1116 engage the gaps between the extensions 1104 such that the collar is prevented from rotating around the center axis of the barrel 110.

Another hypodermic syringe with needle retraction can be found in U.S. Pat. No. 5,336,198, titled "HYPODERMIC SYRINGE WITH NEEDLE RETRACTION FEATURE," which is incorporated in its entirety herein by reference.

While various embodiments of the present invention have been described, it will be apparent to those of skill in the art that many more embodiments and implementations are possible that are within the scope of this invention. Accordingly, the present invention is not to be restricted except in light of the attached claims and their equivalents.

The invention claimed is:

1. A retractable syringe, comprising:
a needle having a tip and a base;
a needle collar coupled to the needle, the needle collar including at least one groove disposed in a bottom portion of the needle collar and extending from the portion of the needle collar nearest to the base of the needle toward the tip of the needle;
a fitting coupled to the needle collar and including a sealing element disposed between a first portion of the fitting and the needle collar;
a barrel unit, the barrel unit designed for coupling to the fitting;
a plunger unit having a piston on a first end of the plunger unit, the plunger unit and piston being positioned in the barrel unit;
an extractor element coupled to the first end of the plunger unit and having a proximal end adjacent to the plunger unit and a distal end, the extractor element designed for coupling to the needle collar and encompassing at least a portion of the at least one groove.

2. The syringe of claim 1, wherein the fitting is a Luer nut that is designed for removable coupling to the barrel unit.

3. The syringe of claim 2, wherein the Luer nut is coupled to the barrel unit by a threaded connection.

4. The syringe of claim 2, wherein the Luer nut is coupled to the barrel unit by a flange.

5. The syringe of claim 1, wherein the at least one groove is located in a lower portion of the needle collar below where the needle collar engages the sealing element.

6. The syringe of claim 1, wherein the sealing element is a wiper seal.

7. The syringe of claim 1, wherein the sealing element is an O-ring.

8. The syringe of claim 7, wherein
the needle collar has an upper portion and a lower portion with a neck portion separating the upper portion from the lower portion, and
the neck portion of the needle collar engages the O-ring to form a seal.

9. The syringe of claim 1, wherein the needle collar includes a channel sized to accommodate the needle such that the needle is coupled to the needle collar.

10. The syringe of claim 1, wherein the barrel unit includes a plurality of bumps arranged in a first row on an inner surface of the barrel unit on an end of the barrel unit farthest from the needle.

11. The syringe of claim 10, wherein each of the bumps is tapered away from the needle.

12. The syringe of claim 10, wherein the barrel unit includes a plurality of bumps arranged in a second row on the inner surface of the barrel unit between the end of the barrel unit farthest from the needle and the first row of bumps.

13. The syringe of claim 12, wherein the barrel unit includes a plurality of bumps arranged in a third row on the inner surface of the barrel unit between the end of the barrel unit farthest from the needle and the second row of bumps.

14. The syringe of claim 13, wherein the bumps in the third row are higher than the bumps in the first row and the bumps in the second row.

15. The syringe of claim 13, wherein the bumps in the second row are higher than the bumps in the first row.

16. The syringe of claim 1, wherein the fitting is a first fitting and further comprising:
a second fitting having an opening on one end and a plastic tube coupled to an end opposite the end having the opening,
wherein,
the opening in the second fitting is configured to accommodate a portion of the first fitting such that the needle extends through the second fitting and the plastic tube to expose a sharp end portion of the needle.

17. The syringe of claim 16, wherein the second fitting is designed for use as a catheter.

18. The syringe of claim 16, wherein the second fitting is designed for coupling to an IV tube connector.

19. The syringe of claim 1, wherein the barrel unit is sized to deliver a maximum of 1 cc of fluid.

20. The syringe of claim 1, wherein the barrel unit is sized to deliver a maximum of ½ cc of fluid.

21. The syringe of claim 1, wherein the piston is tapered towards the needle.

22. The syringe of claim 1, wherein the extractor element is configured to engage the needle collar and extract the needle collar together with the needle through the fitting.

23. The syringe of claim 1 wherein
the needle collar has an upper portion and a lower portion with a neck portion separating the upper portion from the lower portion, and
the neck portion of the needle collar expands the sealing element to form a seal between the needle collar and sealing element.

24. The syringe of claim 23, wherein the neck portion of the needle collar is positioned at an end of the upper portion closest to the lower portion.

25. The syringe of claim 24, wherein a cross sectional width of the neck portion of the needle collar is wider than a cross sectional width of each of the upper portion and the lower portion of the needle collar.

26. The syringe of claim 23, wherein the neck portion of the needle collar includes a lower end, a central portion and an upper end where the central portion of the needle collar tapers towards the lower end where it meets a shaft connecting the upper portion to the lower portion.

27. The syringe of claim 26, wherein the central portion includes a section that tapers towards the upper end where it meets the upper portion.

28. The syringe of claim 23 including at least one groove on at least one side surface of the lower portion of the needle collar.

29. The syringe of claim 1 wherein the fitting is removably coupled to the needle collar.

30. A syringe, comprising:
a needle having a tip and a base;
a needle collar coupled to the needle, the needle collar including at least one groove disposed in a bottom portion of the needle collar and extending from the portion of the needle collar nearest to the base of the needle toward the tip of the needle;
a Luer nut coupled to the needle collar and including a sealing element disposed between a first portion of the Luer nut and the needle collar;
a barrel unit, the barrel unit sized to hold about 1 cc or less of fluid and designed for coupling to the Luer nut;
a plunger unit having a piston on a first end of the plunger unit, the plunger unit and piston being positioned in the barrel unit;
an extractor element coupled to the first end of the plunger unit and having a proximal end adjacent to the plunger unit and a distal end, the extractor element designed for coupling to the needle collar and encompassing at least a portion of the at least one groove.

31. The syringe of claim 30 wherein a flange on the barrel unit engages a flange on the Luer nut to couple the Luer nut to the barrel unit.

32. The syringe of claim 31, wherein the flange of the barrel unit and the flange of the Luer nut are welded together.

33. The syringe of claim 31, wherein the flange of the barrel unit and the flange of the Luer nut are coupled by an adhesive.

34. The syringe of claim 31, wherein the flange of the barrel unit and the flange of the Luer nut are prevented from separating by opposing ridges.

35. The syringe of claim 31, wherein the flange of the barrel unit and the flange of the Luer nut are prevented from separating by friction.

36. The syringe of claim 30 wherein the Luer nut is removably coupled to the needle collar.

37. A needle extraction unit comprising:
a needle collar having an upper portion, a lower portion and a neck positioned between the upper portion and the lower portion;
a fitting coupled to the upper portion of the needle collar and including a sealing element disposed between a first portion of the fitting and the neck of the needle collar;
an extractor element coupled to a first end of a plunger and having a proximal end adjacent to the plunger and a distal end, the extractor element having an opening on the distal end configured to engage the upper portion of the needle collar,
wherein,
the needle collar includes a central channel extending through a length of the needle collar and which is sized to accommodate a needle, and
the neck of the needle collar expands a seal of a Luer nut to form a seal.

38. The extraction unit of claim 37, wherein the fitting is a Luer nut that is designed for removable coupling to a barrel.

39. The extraction unit of claim 37, wherein at least one groove is located in the upper portion of the needle collar below where the needle collar engages the seal.

40. The extraction unit of claim 37, wherein the sealing element is a wiper seal.

41. The extraction unit of claim 37, wherein the sealing element is an O-ring.

42. The extraction unit of claim 37, wherein a cross sectional width of the neck of the needle collar is wider than a cross sectional width of each of the upper portion and the lower portion of the needle collar.

43. The extraction unit of claim 37, wherein the neck of the needle collar includes a lower end, a central portion and an upper end where the central portion of the needle collar tapers towards the lower end where it meets a shaft connecting the upper portion to the lower portion.

44. The extraction unit of claim 43, wherein the central portion includes a section that tapers towards the upper end where it meets the upper portion.

45. The extraction unit of claim 37 wherein the fitting is removably coupled to the upper portion of the needle collar.

46. A syringe for administering insulin including:
- a needle having a tip and a base;
- a needle collar coupled to the needle, the needle collar including at least one groove disposed in a bottom portion of the needle collar and extending from the portion of the needle collar nearest to the base of the needle toward the tip of the needle;
- a Luer nut removably coupled to the needle collar and including a sealing element disposed between a first portion of the Luer nut and the needle collar;
- a barrel unit, the barrel unit designed for coupling to the Luer nut;
- a plunger unit having a piston on a first end of the plunger unit, the plunger unit and piston being positioned in the barrel unit;
- an extractor element coupled to the first end of the plunger unit and having a proximal end adjacent to the plunger unit and a distal end, the extractor element designed for coupling to the needle collar and encompassing at least a portion of the at least one groove.

47. A syringe, comprising:
- a needle having a tip and a base;
- a needle collar coupled to the needle, and having at least one groove extending from an end of the needle collar closest to the base of the needle in a direction toward the tip of the needle;
- a fitting removably coupled to the needle collar;
- a barrel unit having a collar unit on one end;
- a sleeve unit coupled to the collar unit and to the fitting;
- a plunger unit having a piston on a first end of the plunger unit, the plunger unit and piston being positioned in the barrel unit;
- an extractor element coupled to the first end of the plunger unit and having a proximal end adjacent to the plunger unit and a distal end, the extractor element designed for coupling to the needle collar and encompassing at least a portion of the at least one groove.

48. The syringe of claim 47, wherein the collar unit includes a plurality of collar extension units on an inner surface of the collar unit that are each separated by a plurality of gaps; and
the sleeve unit includes a plurality of sleeve extension units on an inner surface of the sleeve unit that are each separated by a plurality of gaps.

49. The syringe of claim 48 including
the collar extension units are arranged such that each collar extension unit engages a gap between the sleeve extension units and the sleeve extension units are arranged such that each sleeve extension unit engages a gap between the collar extension units.

50. The syringe of claim 49 wherein the sleeve unit includes a plurality of ridges on an inner surface of the sleeve unit which are configured to engage a tab on the fitting.

51. The syringe of claim 49 wherein the syringe is a 1 cc syringe.

52. The syringe of claim 47, wherein the fitting is a Luer nut.

* * * * *